United States Patent [19]

Neumann

[11] Patent Number: 5,318,512

[45] Date of Patent: Jun. 7, 1994

[54] BLOOD SEPARATION DEVICE

[75] Inventor: Hans-Jürgen Neumann, Wendel-Niederkirchen, Fed. Rep. of Germany

[73] Assignee: Fresenius AG, Bad Homburg v.d.H.

[21] Appl. No.: 939,672

[22] Filed: Sep. 3, 1992

[30] Foreign Application Priority Data

Sep. 6, 1991 [DE] Fed. Rep. of Germany ....... 4129639

[51] Int. Cl.⁵ .......................................... A61M 37/00
[52] U.S. Cl. .................................................... 604/6
[58] Field of Search ...................................... 604/4–6, 604/34, 250; 210/739, 741, 782

[56] References Cited

U.S. PATENT DOCUMENTS

| | | | |
|---|---|---|---|
| 3,489,145 | 1/1970 | Judson et al. | 604/6 |
| 4,185,629 | 1/1980 | Cullis et al. | 604/6 |
| 4,460,353 | 7/1984 | Deckert et al. | 604/34 X |
| 4,553,963 | 11/1985 | Young | 604/34 X |
| 4,605,503 | 8/1986 | Bilstad et al. | 604/6 X |
| 4,827,970 | 5/1989 | Sugiasaki et al. | 604/250 X |
| 4,897,189 | 1/1990 | Greenwood et al. | 604/5 X |
| 4,911,703 | 3/1990 | Lysaght et al. | 604/6 |
| 4,968,295 | 11/1990 | Neumann | 210/782 X |
| 5,112,298 | 5/1992 | Prince et al. | 604/6 |
| 5,147,290 | 9/1992 | Jonsson | 604/6 X |
| 5,186,431 | 2/1993 | Tamari | 604/34 X |

FOREIGN PATENT DOCUMENTS 3931471  4/1991  Fed. Rep. of Germany .

OTHER PUBLICATIONS

McLead, et al., "Plateletpheresis With the COBE Spectra Single Needle Access Option," Journal of Clinical Apheresis, vol. 6, pp. 24–27, (1991).

Primary Examiner—C. Fred Rosenbaum
Assistant Examiner—Frank Wilkens
Attorney, Agent, or Firm—Marshall, O'Toole, Gerstein, Murray & Borun

[57] ABSTRACT

Device for the separation of blood with a cannula with the aid of separation in a centrifuge with a blood pump in an inlet line and a collection storage bag, which can be emptied with the aid of a pressure device into a return line. The flow resistance $R_o$ of the return line is designed so that it has preferably about half of the flow resistance of the remainder of the return system. In a return/recirculation phase, the blood pump is operated at a predetermined recirculation flow rate $F_R$, whereby a predetermined cannula infusion flow rate $F_N$ is established as a function thereof.

5 Claims, 5 Drawing Sheets

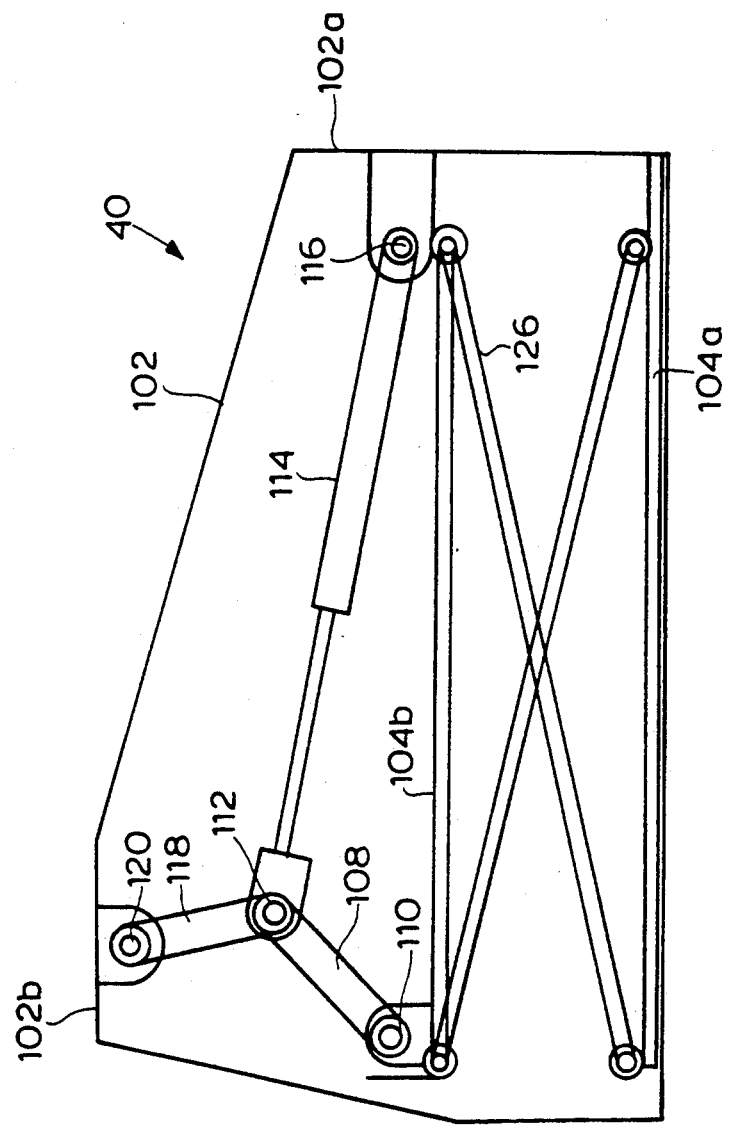

BLOOD SEPARATION DEVICE

BACKGROUND OF THE INVENTION

1. Field of the Invention

The invention is concerned with a device for the separation of blood and, more specifically the invention is concerned with a device for the separation of blood with a cannula using a single needle, with recirculation.

2. Description of Related Technology

A blood separation device of the type mentioned above is known, for example, from DE-OS 39 31 471 (published Apr. 11, 1991) or the Journal of Clinical Apheresis, Volume 6, pages 24–27 (1991), the respective disclosures of which are incorporated by reference herein.

In comparison to the continuous two-needle method, the single-needle method provides the advantage that the donor has to be punctured with a cannula only once. This is especially advantageous when the puncturing conditions are poor.

On the other hand, in the single-needle method, two cycles must be performed. In a collection cycle, blood is drawn from a vein and introduced into a centrifuge for separation, where the blood fractions to be collected and recycled are separated. In a return cycle, the fractions to be returned to the donor are transported back, for example, with the aid of a second pump, as described in the DE-OS 39 31 471 or with the aid of a device that exerts pressure on a storage bag.

Two problems arise in the single-needle method, namely intolerance to the anticoagulant added to the blood, which depends on the patient, and the partially limited effectiveness of the separation.

Firstly, blood donors exhibit different tolerance to anticoagulant, which is mostly added in the form of ACD-A, upon return to the vein of the arm. At high blood return flow rates, large amounts of anticoagulant are returned to the donor. On the other hand, at low return rates, the time required for return is lengthened correspondingly. Therefore, it is desirable to have the possibility of adjusting the return flow rate.

As mentioned in DE-OS 39 31 471, the partially limited effectiveness of the separation can be improved by recirculation of the return blood. However, DE-OS 39 31 471 does not disclose what control means are used in the case of the blood pump used therein being used as a return pump and in the case of the second pump that is included in the return circuit thereof.

SUMMARY OF THE INVENTION

Therefore, according to the invention, the blood collection device of the prior art is improved so that, on the one hand, a predetermined amount of blood can be returned to the patient to improve the patient's tolerance to anticoagulant and, on the other hand, the effectiveness of the separation can be increased.

Firstly, the blood separation device of the invention requires only a single pump in the form of a blood pump in the inlet/recirculation branch, while the return branch includes a pressure device which exerts a pressure on a storage bag, against the pressure of which the storage bag is filled in the collection phase. The pressure device advantageously exerts a constant pressure on the storage bag in the return phase. A suitable pressure device is described in German patent application No. P 41 29 271.5 filed Sep. 3, 1991 and entitled "Device for Emptying Flexible Liquid Containers," the disclosure of which is incorporated herein.

Consequently, in the return phase, a passive pressure device is employed, rather than an active return pump operating with a predetermined transport phase, so that the total fluid resistance existing in the return system determines the amount of blood returned to the patient.

Usually, the return system comprises or consists of three components, namely a bag, including a connecting line to a return line, the return line leading to a Y-piece, and a line leading away from the Y-piece, including the cannula or needle itself.

Thus, the total fluid resistance consists of the partial fluid resistances $R_p$ for the internal resistance of the bag, including the connecting line, $R_o$ for the return line resistance, and $R_N$ for the cannula (needle) resistance. The partial resistances add up to the total resistance $R_{TOT}$.

According to the invention, the flow resistance $R_o$ of the return line is 0.2–0.8 times, and preferably about 0.5 times that of the total resistance $R_{TOT}$, where "about" means a deviation of ±20%. With such a ratio, the cannula reinfusion flow $F_N$ can be adjusted in the medically appropriate limits of 50–80 ml/minute, whereby, at the same time, the recirculation rate $F_R$ can be adjusted in the range from 20–80 ml/minute, which is technically appropriate for the centrifuge. In addition, in such a case, the pressure $P_o$ is about 100 mm Hg, determined by the bag pressure device.

These parameters give the following straight line equation:

$$F_N = 1/R_{TOT}(P_o - R_o R_R) \tag{1}$$

FIG. 3 shows the straight line relationship for the flow rates $F_N$ and $F_R$, the slope of the lines being determined by the ratio of $R_o/R_{TOT}$, which assumes a preferred value of about 0.5 according to the invention.

The value of $R_o$ or the ratio $R_o/R_{TOT}$ can be determined simply from the above straight line equation (1). Firstly, the flow rate of the blood pump can be predetermined. On the other hand, with the aid of suitable flowmeters, the reinfusion or return flow rate $F_N$ into the cannula can be directly determined. If the pressure exerted by the pressure device is constant, then the slope of the straight lines can be determined from FIG. 3, that is, the ratio $R_o/R_{TOT}$ can be adjusted within certain limits. Thus, $R_o$ can be increased by activating an adjustable clamp or choke in the return line, which increases or decreases the resistance to flow. Naturally, similarly, a predetermined tube system with a given inside diameter and a given length, that is, with a predetermined flow resistance, can be used. Finally, naturally, the flow resistance of the rest of the return system, especially the cannula resistance, can be adjusted by choosing different needle sizes. However, usually, the flow resistance of the return line is changed with an adjustable clamp, or a preselected tube is used. Thus, for example, a tube that can be used for blood cell separation with an inside diameter of about 3 mm and the length and tube segments used there can be employed advantageously.

Considering the relationships shown in FIG. 3, it can be seen that, without recirculation ($F_R = 0$), a reinfusion flow rate of 90 ml/minute can be reached, which can be achieved only by adjusting the total resistance.

On the other hand, by activation of the blood pump as a recirculation pump, different reinfusion flow rates can be achieved as was demanded at the beginning. For example, at a recirculation flow rate of 80 ml/minute, a reinfusion flow rate of 50 ml/minute can be achieved. Naturally, this reinfusion flow rate lasts only until the storage bag is emptied, whereupon a new collection cycle begins.

Besides, it should be pointed out that the reinfusion flow is determined not only by the pressure on the storage bag, but rather, it is also dependent on the hematocrit value and on the viscosity of the blood. However, the latter parameter should be regarded as largely constant during treatment.

The amount of the tolerable anticoagulant flow rate through the return line depends on the size, weight and sex of the donor. Thus, a small, light female donor can tolerate significantly less anticoagulant per unit time than a large, heavy male donor. According to the invention, a reference table can be used for these relationships and, at the same time, the hematocrit and the viscosity can also be taken into consideration. Advantageously, according to the invention, such a table is programmed in the control means of the inventive device. Such an adjustment can be carried out by the microprocessor of the cell separator itself, into which this table and the specific values of the donor can be entered. Thus, the microprocessor selects a recirculation flow rate as a function of the hematocrit, size, weight and sex of the donor so that the safety limit is not exceeded during reflux into the donor. According to the invention, this is achieved essentially at the flow rates given at the outset.

The recirculation carried out according to the invention in the single-needle method of blood collection and separation leads to a broader and thus improved separation of the blood components to be separated, especially thrombocytes. For example, if, in a five-minute collection phase, about 50% of the thrombocytes of the processed blood are collected in the collection bag, in the return phase, with five-minute recirculation period, another 50% of the remaining thrombocytes can be harvested, so that a total of 75% of all separable thrombocytes will be separated.

The higher the recirculation flow rate and the longer the reinfusion, the greater the increase in effectiveness, and vice versa.

As referred to above, the return flow can be adjusted at a constant recirculation rate by changing the flow resistance of the return line, for example, by using a commercial roller clamp.

Depending on the compatibility of the anticoagulant with the donor, the maximum return flow rate can be determined largely by the selection of the cannula. At the same recirculation flow rate, using a thin cannula, the reinfusion flow to the donor will be less than in the case for a thicker one. The determined values can be read from a diagram for various cannulas and return flow rates.

DETAILED DESCRIPTION OF A PREFERRED EMBODIMENT

Other advantages of the invention are presented in the description of a preferred embodiment, below.

FIG. 8 is a schematic representation of the pressure device of FIG. 4 showing the fixed and movable plates being joined by a scissors guide.

Figure 1:
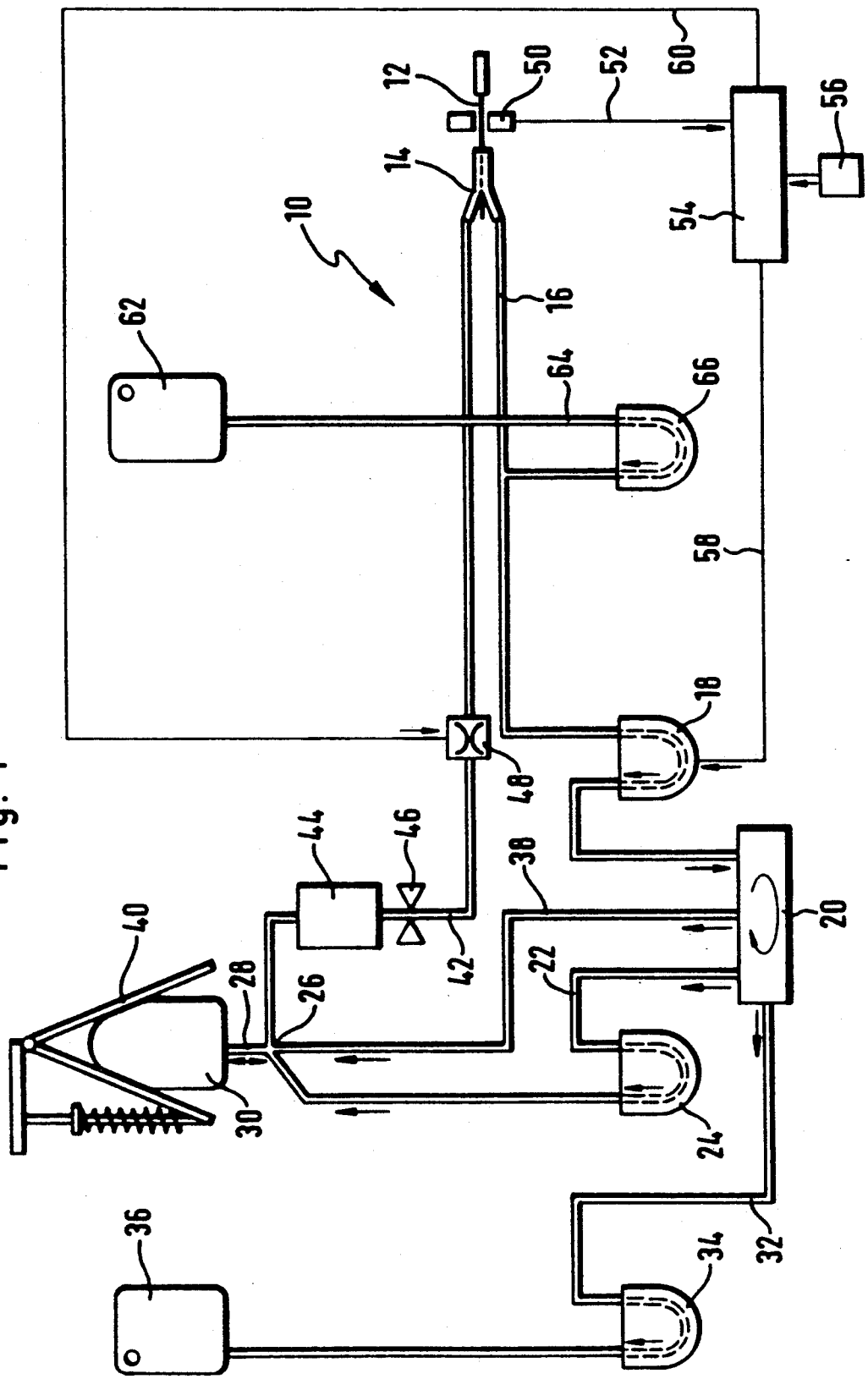
FIG. 1 shows a schematic arrangement of a single-needle arrangement according to the invention.

In FIG. 1, a blood collection and separation device 10 of the invention has a cannula 12 to be connected at one end to a patient and at the other end to a Y-piece 14. An inlet/recirculation line 16 extends from the Y-piece and contains a blood pump 18. The line 16 is connected to a centrifuge or separation device 20, in which a separation chamber (not shown) is disposed.

A plasma line 22 extends from the centrifuge and contains a plasma pump 24. The plasma line 22 is connected through a branched connector 26 and a connecting line 28 to a collection/storage bag 30.

A thrombocyte line 32 containing a thrombocyte pump 34 extends from the centrifuge 20 to a thrombocyte collecting bag 36.

Finally, an erythrocyte line 38 extends from the centrifuge 20 through the branched connector 26 and the connecting line 28 to the storage bag 30.

The collection/storage bag 30 is disposed within a pressure device 40, which exerts a predetermined pressure on the bag 30 which is substantially independent of the degree of filling of the storage bag 30. The pressure device 40 is described more fully below with respect to FIGS. 4–8.

From the branched connector 26, a return line 42 leads to the Y-piece 14. In the illustrated embodiment, a drip chamber 44, a clamp 46, and a choke or clamp 48 are disposed in the return line 42 in order to allow the cross section of the return line 42 to be varied.

Finally, a flowmeter apparatus 50 is provided in the vicinity of the cannula 14 to provide a signal through a conductor 52 to recirculation control equipment 54. The recirculation control equipment 54 is connected to an input device 56 and controls the blood pump 18 through conductors 58 and 60 and, optionally, the choke 48 in the recirculation phase.

For the sake of clarity, another controller with which the single-needle apparatus is switched between the separation and return cycles is not shown.

Figure 2:
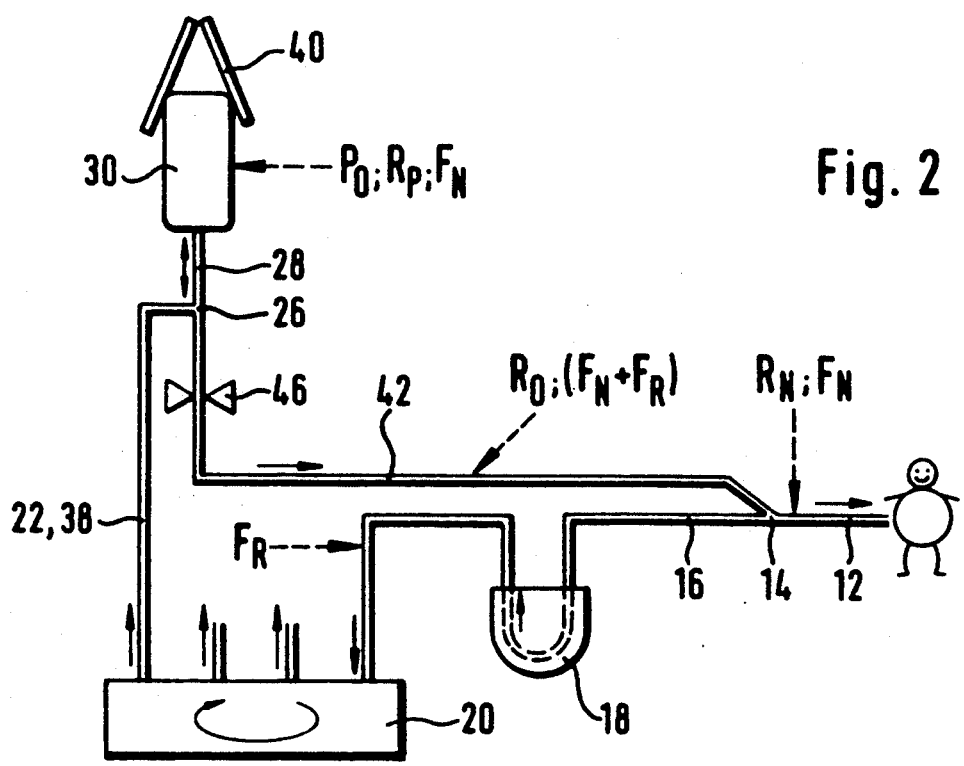
FIG. 2 is another schematic arrangement of the device according to FIG. 1 shown in a return/recirculation phase.
Figure 3:
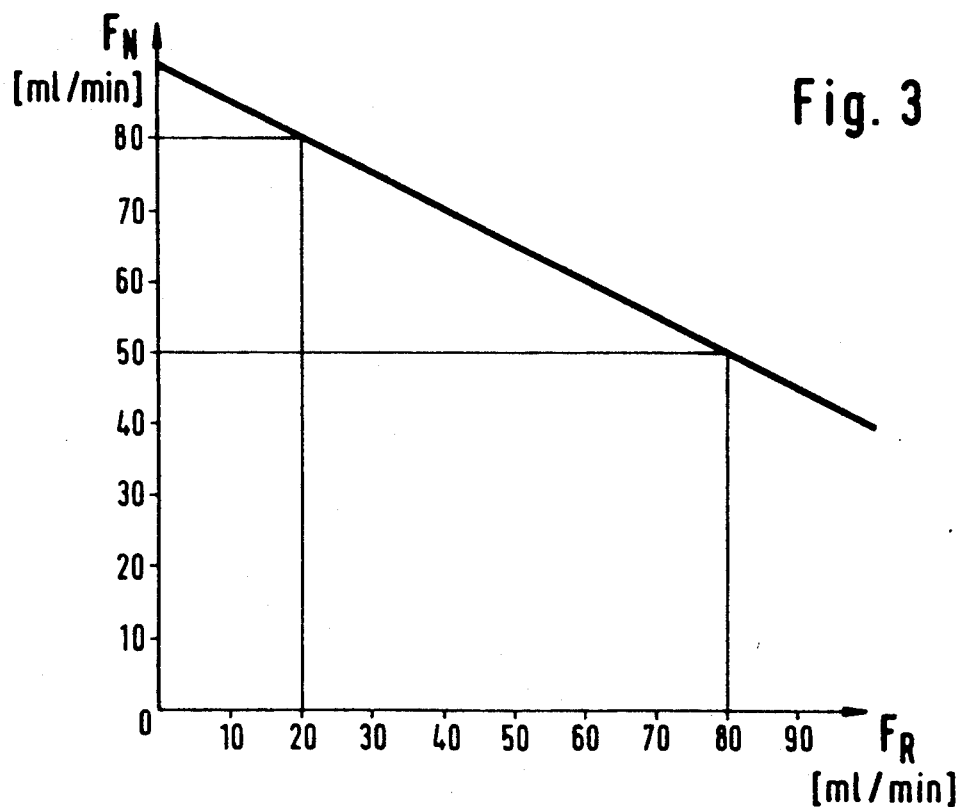
FIG. 3 is a graphical representation in which the dependence of the cannula reinfusion flow on the recirculation flow rate is shown when the device of the invention is used.

In FIG. 2, the same reference numbers are used for the same elements as in FIG. 1. In addition, the following parameters are shown for the individual elements:

$R_N$ = cannula (needle) resistance
$R_o$ = return line resistance
$R_P$ = internal resistance of the pressure device and connecting line
$F_R$ = recirculation flow rate
$F_N$ = cannula (needle) flow rate
$P_o$ = pressure device pressure The parameters depend on one another according to equation (1), above.

The device of FIG. 1 is operated as follows.

A tube system is chosen in which $R_o$ is about half of the total resistance consisting of $R_N$, $R_o$, and $R_P$. If desired, by measurement with a flowmeter and setting of the choke 48 according to the evaluation, the choke 48 is set by the recirculation control device 54 (i.e., the tube diameter is either widened or narrowed).

Through the input device 56, the patient-specific data as well as attempted cannula and recirculation flow rates can be entered. Using the algorithm of equation (1), the computer in the control device 54 can adjust the recirculation rate of the blood pump 18 and, if desired, the choke 48 as well, to change the resistance of the return line 42.

The operation of the single-needle device 10 itself is done, for example, as described in DE-OS 39 31 471. Thus, in the collection phase, the blood pump 18 is first activated during which clamp 46 remains closed. At the same time, the pump 66 is started in order to introduce the anticoagulant. The individual blood components separated in the centrifuge 20 are removed with the aid of the plasma pump 24 and the thrombocyte pump 34, respectively whereby, additionally, the blood pump 18 transports the erythrocytes into the collection/storage bag 30, where they are mixed again with plasma.

After completion of the collection phase, the return phase begins with the recirculation step. For this purpose, the clamp 46 is opened and the blood pump 18 is operated at the transport rate for recirculation. Since the blood already contains anticoagulant, the anticoagulant pump 66, which transports the anticoagulant from an anticoagulant bag 62 through a line 64 to the inlet/recirculation line 16, is stopped. On the other hand, the plasma pump 24 and the thrombocyte pump 34 continue to operate.

After completion of the return phase and recirculation, the equipment is switched again to the collection/separation cycle, during which blood drawn from the patient through inlet 16 is introduced to the centrifuge 20.

Thus, with the aid of the device 10 according to the invention, using recirculation, the amount of anticoagulant returned to the patient per unit time can be reduced, and, moreover, the effectiveness of the separation can be increased.

Figure 4:
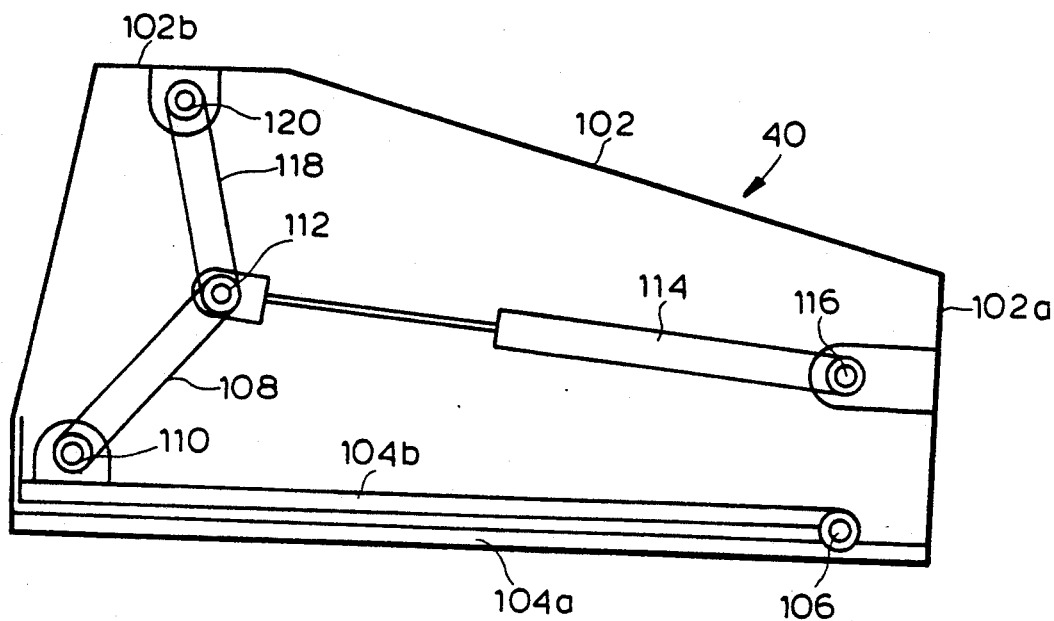
FIG. 4 is a schematic representation of a pressure device according to the invention, shown in a position in which a collection/storage bag (not shown) is drained.

FIG. 4 is a schematic representation of a preferred embodiment of a pressure device 40 according to the invention. Disposed within a housing 102 are a force member 114, a movable plate 104b and a fixed plate 104a, force transfer means 108 and 118 and the collection/storage bag 30 (not shown in FIG. 4).

The housing 102 incorporates first a fixed plate 104a and a movable plate 104b which pivots in a range of 0° to a maximum 90° about a hinge 106 relative to the fixed plate 104a, with a preferable pivot range of 0° to 25°.

A first lever arm 108 is attached to the movable plate 104b and mounted for pivotable movement about a hinge 110. The other end of the lever arm 108 is connected to a hinge point 112 which is acted upon at a variable angle by a force member 114, in this case a gas-pressure spring. The end of the force member disposed opposite the hinge point 112 is attached by a support hinge 116 to the inner wall 102a of the housing. The hinge point 112 is further acted upon by a second lever arm 118 which is also mounted for pivotable movement about the hinge point 112, and which also has an opposite end attached by a hinge 120 to the upper wall 102b of the housing to be acted on at a variable angle by the force member 114.

The force member 114 and the force transfer means 108 and 118 cooperate in such a way that, as the collection/storage bag 30 is being drained, force is applied by the force member 114 through the gas-pressure cylinder piston to the hinge point 112. The applied force moves the lever arms 108 and 118 from their rest positions and the latter force the movable plate 104b in the direction of the fixed plate 104a. This in turn causes pressure to be applied to the collection/storage bag 30. The force applied by the force member 114 to the force transfer means 108 and 118 and which is deflected to the movable plate 104b and correspondingly to the collection/storage bag 30, varies due to the variable angle of the movable hinge point 112 relative to the hinge 120, the hinge 110 and the force member 114 mounted at the support hinge 116 in accordance with fluid level in the collection/storage bag 30, in that as the fluid level drops the force applied by force member 114 to the force transfer means 108 and 118 maintains a steady pressure on the collection/storage bag 30 as a result of the intensified leverage effect of the force transfer means. Lever arms 108 and 118 which are actuated by force member 114 are pivoted toward one another, regardless of the amount of force applied to them, at an angle of between 0° and a maximum of 180°, but preferably between 25° and 75°.

Figure 5:
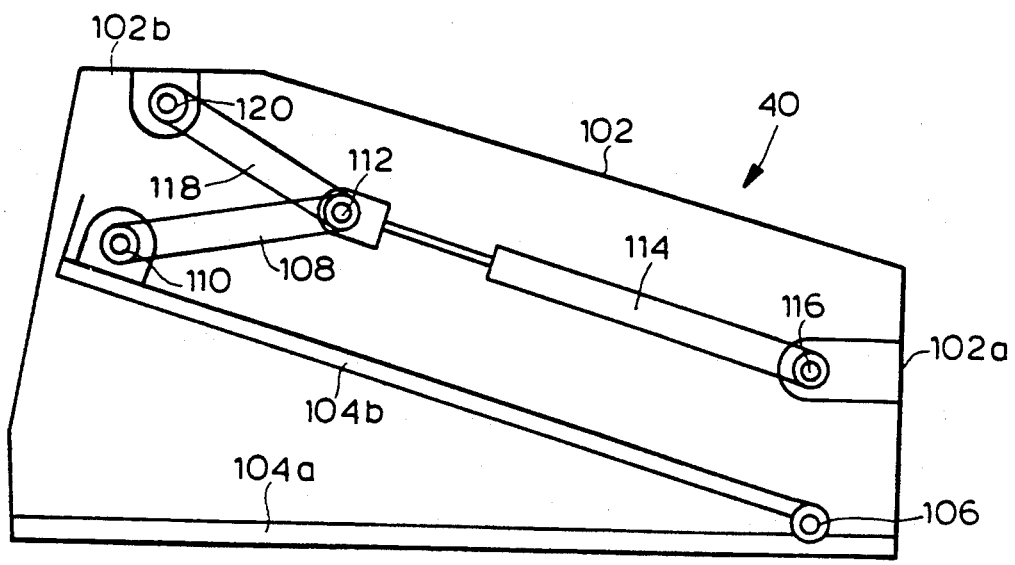
FIG. 5 is a schematic representation of the pressure device of FIG. 4, shown in a position in which a collection/storage bag (not shown) is filled.

FIG. 5 shows the same embodiment of FIG. 4 but with a filled collection/storage bag 30 (not shown here). When the bag is full, the degree of force exerted by the pressurized force member against the hinge point 112 is only slightly varied by an initial minimal deflection of the lever arms 108 and 118. The angle between the levers 108 and 118 is at this point smaller than when the bag is almost completely drained (cf. FIG. 1).

Figure 6:
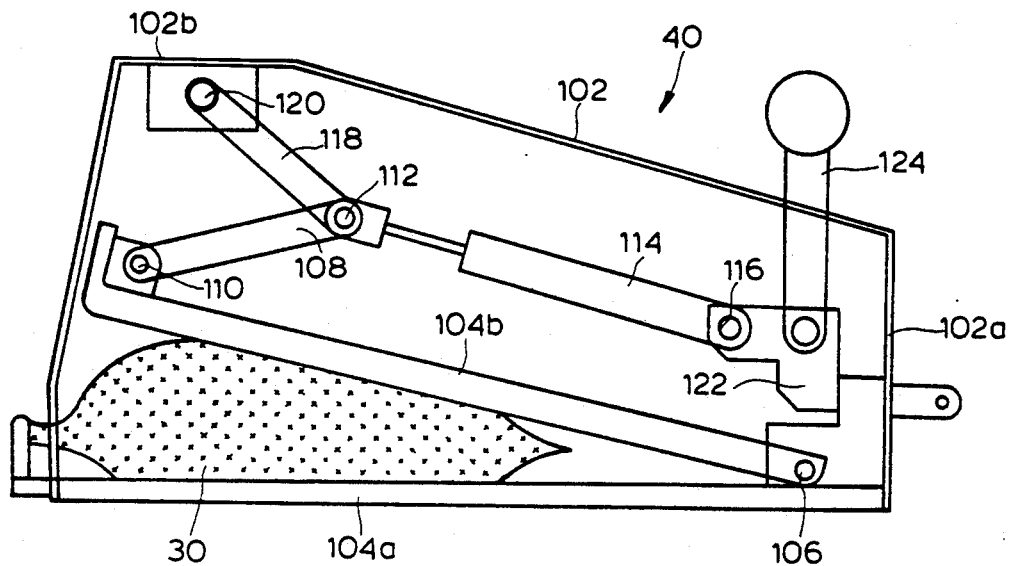
FIG. 6 is a schematic representation of the pressure device of FIG. 4 including a locking mechanism in an opened position.

The embodiment of the pressure device shown in FIG. 6 includes force members, plates and force transfer means identical to the force members, plates and force transfer means shown in FIGS. 4 and 5. With regard to their operation, therefore, reference is made to the foregoing descriptions.

In addition to the elements shown in FIGS. 4 and 5, the pressure device of FIG. 6 also includes a locking mechanism for the force member 114 and the force transfer means 108 and 118, shown here in the unlocked position. It consists of a locking lever 124 which actuates the locking mechanism and a second lever 122 which, upon actuation of the locking lever 124, pivots the force member 114 and the force transfer means 108 and 118 out of their rest positions, thereby preventing them from exerting any pressure on the movable plate 104b and, correspondingly, on the collection/storage bag 30.

Figure 7:
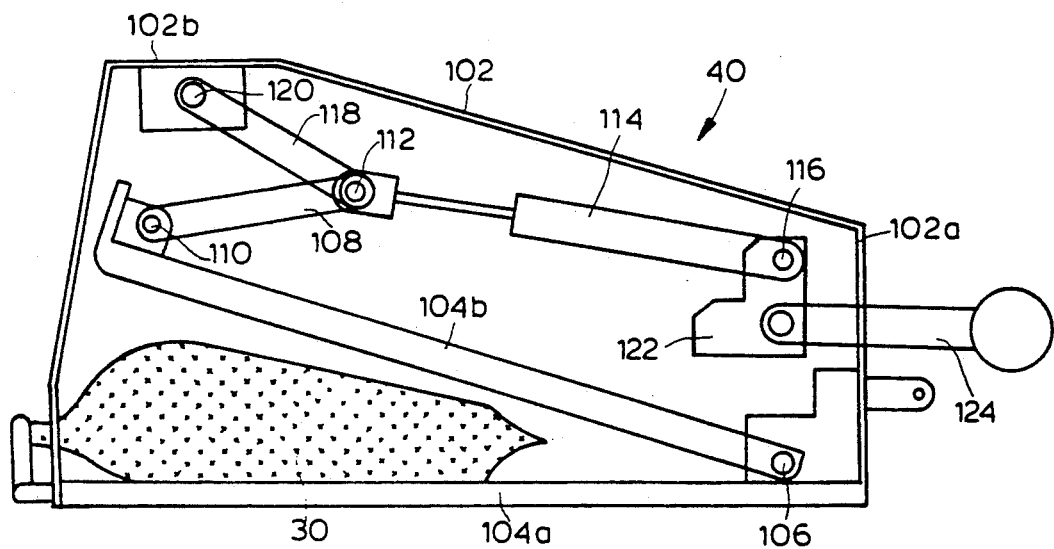
FIG. 7 is a schematic representation of the pressure device of FIG. 6 with the locking mechanism shown in an engaged position.

FIG. 7 shows the identical locking mechanism in the locked position. By actuating the locking lever 124 the force member 114 and the force transfer means 108 and 118 are pivoted far enough out of their rest positions to prevent the gas-pressure spring 114 from exerting pressure on the lever arms 108 and 118, such that the movable plate 104b would not be deflected far enough to apply pressure to the collection/storage bag 30.

FIG. 8 shows the same embodiment of the pressure device as FIGS. 4 and 5 with the following exception: The fixed plate 104a and movable plate 104b are connected by a scissors guide 126.

Further embodiments of the pressure device may include multiple scissors guides between the fixed and movable plates, or both plates may be connected to one another by single or multiple parallel guide means.

The foregoing detailed description is given for clearness of understanding only, and no unnecessary limitations should be understood therefrom, as modifications within the scope of the invention will be apparent to those skilled in the art.

I claim:

1. Device for the separation of blood, comprising a cannula to be connected to a patient, a Y-piece connected to the cannula, an inlet line extending from the Y-piece, a blood pump disposed in said inlet line, a centrifuge connected to said inlet line and comprising a separation chamber, a plasma removal line extending from said separation chamber to a first collection/storage bag for collection of plasma and erythrocytes, a plasma pump disposed in said plasma removal line, a thrombocyte removal line extending from said separation chamber to a thrombocyte collection bag, a thrombocyte pump disposed in said thrombocyte removal line, a return line having a flow resistance $R_o$, said return line connected to said first collection/storage bag by a connecting line and extending from said connecting line to said Y-piece, an anticoagulant supply connected to said inlet line through a supply line containing an anticoagulant pump, a pressure device that exerts pressure on said first collection/storage bag to return erythrocytes and plasma mixture therefrom, said first collection/storage bag, said return line, said connecting line, said Y-piece and said cannula defining a return system, control means for alternately activating said blood pump, anticoagulant pump and thrombocyte pump on the one hand and said return system on the other hand, between a collection phase and a return phase, characterized in that the flow resistance $R_o$ of said return line is 0.2 to 0.8 times the flow resistance of the total return system, that the pressure device is set to a predetermined pressure $P_o$ and that, in said return phase, the blood pump returns a portion of the recycled erythrocyte and plasma mixture at a predetermined transport rate through said inlet line to said centrifuge.

2. The device of claim 1 wherein said flow resistance $R_o$ of said return line is 0.5 times the flow resistance of the total return system.

3. The device of claim 1 wherein at a predetermined pressure $P_o$ of about 100 mm Hg, the flow rate $F_N$ of said cannula is 50 or 80 ml/minute at a predetermined recirculation flow rate $F_R$ of 80 or 20 ml/minute respectively, whereby the recirculation flow rate $F_R$ is correlated with the cannula flow rate $F_N$ according to the equation $$F_N = 1/R_{TOT}(P_o - R_o F_R)$$

wherein $R_{TOT} = R_N + R_o R_p$, wherein $R_N$ is cannula resistance and $R_p$ is the internal resistance of the pressure device and connecting line and wherein an adjustable choke is disposed in said return line with which said flow resistance $R_o$ of said return line can be adjusted.

4. The device of claim 3 wherein a flowmeter is disposed near said cannula and produces a signal used by a recirculation control device according to said equation for activation of one or both of said choke and said blood pump.

5. The device of claim 4 wherein said recirculation control device is provided with an input unit with which patient-specific data and the flow rates of the cannula and blood pump can be entered.

* * * * *